(12) United States Patent
Sampson et al.

(10) Patent No.: US 8,232,360 B2
(45) Date of Patent: Jul. 31, 2012

(54) STEREOREGULAR ROMP POLYMERS

(75) Inventors: Nicole S. Sampson, Setauket, NY (US);
Kathlyn A. Parker, Setauket, NY (US)

(73) Assignee: Research Foundation of State University of N.Y., Albany, NY (US)

( * ) Notice: Subject to any disclaimer, the term of this patent is extended or adjusted under 35 U.S.C. 154(b) by 684 days.

(21) Appl. No.: 12/309,503

(22) PCT Filed: Jul. 17, 2007

(86) PCT No.: PCT/US2007/073715
§ 371 (c)(1),
(2), (4) Date: Feb. 10, 2009

(87) PCT Pub. No.: WO2008/019217
PCT Pub. Date: Feb. 14, 2008

(65) Prior Publication Data
US 2011/0251363 A1    Oct. 13, 2011

Related U.S. Application Data

(60) Provisional application No. 60/807,524, filed on Jul. 17, 2006.

(51) Int. Cl.
*C08F 5/00* (2006.01)
*C08F 13/00* (2006.01)

(52) U.S. Cl. ............ 526/171; 526/238.1; 526/304; 560/124; 560/118; 560/123; 530/330; 564/123; 536/53; 536/22.1; 536/23.1; 534/14; 534/15

(58) Field of Classification Search ............ 526/171, 526/238.1, 304; 560/124, 118, 123; 530/330; 564/123; 536/53, 22.1, 23.1; 534/14, 15
See application file for complete search history.

(56) References Cited

U.S. PATENT DOCUMENTS

| | | |
|---|---|---|
| 5,998,326 A | 12/1999 | Hafner et al. |
| 6,063,759 A | 5/2000 | Yatvin et al. |
| 6,322,815 B1 | 11/2001 | Saltzman et al. |
| 6,339,060 B1 | 1/2002 | Yatvin et al. |
| 6,911,535 B2 | 6/2005 | Schwartz |
| 6,992,156 B2 | 1/2006 | Parker et al. |
| 7,026,440 B2 | 4/2006 | Bentley et al. |
| 7,049,285 B2 | 5/2006 | Park |
| 7,053,150 B2 | 5/2006 | Kozlowski et al. |

OTHER PUBLICATIONS

Lee et al., Amino Acid-Bearing ROMP Polymers with a Stereoregular Backbone, JACS 2006, 128, 4578-4579.*

(Continued)

*Primary Examiner* — Robert D. Harlan
(74) *Attorney, Agent, or Firm* — Hoffman & Baron, LLP

(57) ABSTRACT

The invention relates to stereoregular ROMP polymers, the monomers used to make them, and the processes used to convert the monomers to the polymers.

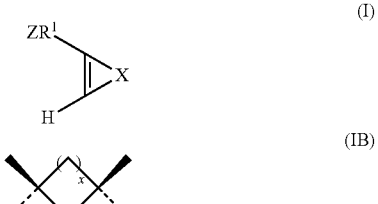

33 Claims, 4 Drawing Sheets

OTHER PUBLICATIONS

Bertin, et al: "Multifunctional Polymeric Nanoparticles from Diverse Bioactive Agents," Journal American Chemical Society, Sep. 16, 2005, 2 pages.

Bertin, et al.: "High-Density Doxorubicin-Conjugated Polymeric Nanoparticles via Ring-Opening Metathesis Polymerization," Chem. Commun., 2005, pp. 3793-3795.

Feng, et al.: "High Regioselectivity in the Ring-Opening Cross-Metathesis of 1-Arylcyclobutene," Eur. J. Org. Chem., 2002, pp. 2942-2947.

Wilson, et al.: "Cyclobutene Derivatives as Isoprene Equivalents in Terpene Synthesis. The Metathesis of 1-Methylcyclobutene," Communications J. Org. Chem., vol. 41, No. 24 (1976), pp. 3928-3929.

Kormer, et al.: "C NMR Spectroscopic Investigation of the Poly(1-methylcyclobutene) Structure," S.V. Lebedev All-Union Synthetic Rubber, Scientific Research Institute, 198035, Leningrad, USSR, Apr. 25, 1980, pp. 531-535.

Katz, et al.: "Metathesis of a Cyclic Trisubstituted Alkene. Preparation of Polyisoprene from 1-Methylcyclobutene," Journal of the American Cancer Socity, 98:2, Jan. 21, 1976, pp. 606-608.

Katz, et al.: "Preparations of Polymers Using Metal-Carbenes," Elsevier Sequoia A.A., Lausanne—printed in Netherlands, pp. 219-226.

* cited by examiner

STEREOREGULAR ROMP POLYMERS

This application asserts priority from U.S. provisional patent application 60/807,524 filed Jul. 17, 2006, the contents of which are incorporated herein by reference.

This invention was funded by the National Institutes of Health under grants HD38519 and CA87503. The United States government has rights in this application.

BACKGROUND

"Living" polymerizations provide materials with well-defined chain lengths and narrow molecular weight distributions (polydispersity indices or PDIs). They also allow the preparation of block polymers. Among the general classes of living polymerizations, ring opening metathesis polymerization (ROMP) has been broadly applied for the synthesis of materials with interesting physical properties[1] and biological activities.[2,3]

Although ROMP polymers have been prepared from many strained cycloalkenes and their derivatives,[4] norbornenes and oxanorbornenes are typically used for the preparation of peptide- and carbohydrate-bearing multivalent ROMP polymers.[3,5] These monomers, substituted on the 5-position or on the 5- and 6-positions of the norbornene ring, are the most synthetically accessible monomers that metathesize efficiently. However, in these systems, stereocontrol of the polymerization reaction is not always possible. For example, ruthenium-catalyzed polymerization of 5-substituted norbornene and oxanorbornene monomers provides stereochemically heterogeneous materials.[6] Each monomeric unit contributes three stereochemical variables that are not controlled in the chain extension step.[7] Therefore it is difficult to correlate the physical or biological properties of these polymers with specific structural features.

The literature offers several examples of the ROMP and ROM (ring opening metathesis) of substituted cyclobutenes[9-12] including three examples in which the substrate is a 1-substituted cyclobutene.[12] Indeed, with the $(CO)_5WC(C_6H_5)_2$ catalyst, Katz and coworkers produced translationally invariant (all head-to-tail, E-olefinic) polymer from 1-methylcyclobutene and from 1-trimethylsilylcyclobutene.[12d] Nonetheless, it was unexpected that the more functional group-tolerant ruthenium catalysts would give analogous results with related monomers that bear functional groups, such as amide functional groups.

Ring opening metathesis polymerization is especially unpredictable when conducted with monomers that are cyclic unsaturated amides, especially those in which a conjugated double bond is in the ring. Neither the regiochemistry of the ring opening nor the geometry of the resulting double bond in the polymer could have been predicted.

REFERENCES FOR BACKGROUND SECTION 1. (a) Komiya, Z.; Pugh, C.; Schrock, R. R. *Macromolecules* 1992, 25, 6586-6592. (b) Royappa, A. T.; Saunders, R. S.; Rubner, M. F.; Cohen, R. E. *Langmuir* 1998, 14, 6207-6214. (c) Lynn, D. M.; Mohr, B.; Grubbs, R. H. *J. Am. Chem. Soc.* 1998, 120, 1627-1628.
2. (a) Gordon, E. J.; Gestwicki, J. E.; Strong, L. E.; Kiessling, L. L. *Chem. Biol.* 2000, 7, 9-16. (b) Gestwicki, J. E.; Cairo, C. W.; Strong, L. E.; Oetjen, K. A.; Kiessling, L. L. *J. Am. Chem. Soc.* 2002, 124, 14922-14933.
3. (a) Roberts, K. S.; Konkar, S.; Sampson, N. S. *ChemBioChem* 2003, 4, 1229-1231. (b) Baessler, K.; Lee, Y.; Roberts, K. S.; Facompre, N.; Sampson, N. S. 2006 *Chem. Biol,* 16, 544-550.
4. Black, G.; Maher, D.; Risse, W. Living Ring-Opening Olefin Metathesis Polymerization. In *Handbook of Metathesis*, vol. 3; Grubbs, R. H., Ed.; Wiley-VCH: Weinheim, 2003; pp 2-71.
5. (a) Nomura, K.; Schrock, R. R., *Macromolecules* 1996, 29, 540-545.; (b) Biagini, S. C. G.; Davies, R. G.; Gibson, V. C.; Giles, M. R. Marshall, E. L.; North, M.; Robson, D. A., *Chem. Commun.* 1999, 235-236. (c) Kiessling, L. L. Owen, R. M. Syntheses and Applications of Bioactive Polymers Generated by Ring-Opening Metathesis Polymerization. In *Handbook of Metathesis*, vol. 3; Grubbs, R. H., Ed.; Wiley-VCH: Weinheim, 2003; pp 180-225.
6. (a) Amir-Ebrahimi, V.; Corry, D. A.; Hamilton, J. G.; Thompson, J. M.; Rooney, J. J., *Macromolecules* 2000, 33, 717-724. (b) Maynard, H. D.; Okada, S. Y.; Grubbs, R. H. *Macromolecules* 2000, 33, 6239-6248.
7. Schueller, C. M.; Manning, D. D.; Kiessling, L. L. *Tetrahedron Lett.* 1996, 37, 8853-8856.
8. Roberts, K. S.; Sampson, N. S. *Org. Lett.* 2004, 6, 3253-5.
9. 3-substituted cyclobutenes: (a) Maughon, B. R.; Week, M.; Mohr, B.; Grubbs, R. H., *Macromolecules* 1997, 30, 257-265; (b) Maughon, B. R.; Grubbs, R. H., *Macromolecules* 1997, 30, 3459-3469.
10. 3,4-disubstituted cyclobutenes: (a) Lapinte, V.; de Fremont, P.; Montembault, V. R.;. Fontaine, L., *Macromol. Chem. Phys.* 2004, 205, 1238-1245; (b) Perrott, M. G.; Novak, B. M., *Macromolecules* 1996, 29, 1817-1823. (c) Snapper, M. L.; Tallarico, J. A.; Randall, M. L. *J. Am. Chem. Soc.* 1997, 119, 1478-1479 and Tallarico, J. A.; Randall, M. L. Snapper, M. L. *Tetrahedron*, 1997, 53, 16511-20.
11. 3,3-disubstituted cyclobutenes: (a) Wu, Z.; Grubbs, R. H. *Macromolecules.* 1995, 28, 3502-3508; (b) Alder, R. W.; Allen, P. R.; Khosravi, E. *J. Chem. Soc., Chem. Commun.* 1994, 1235-1236.
12. 1-substituted cyclobutenes: (a) Katz, T. J.; McGinnis, J.; Altus, C., *J. Am. Chem. Soc.* 1976, 98, 606-608. (b) Wilson, S. R.; Schalk, D. E., *J. Org. Chem.* 1976, 41, 3928-3929. (c) Kormer, V. A.; Dolinskaya, E. R.; Khatchaturov, A. S., *Makromol. Chem. Rapid Commun.* 1980, 1, 531-535. (d) Katz, T. J.; Lee, S. J.; Shippey, M. A., *J. Mol. Catal.* 1980, 8, 219-226. (e) Feng, J.; Szeimies, G., *Eur. J. Org. Chem.* 2002, 2942-2947.
13. Love, J. A.; Morgan, J. P.; Trnka, T. M.; Grubbs, R. H., *Angew. Chem. Int. Ed. Engl.* 2002, 41, 4035-4037.

SUMMARY OF THE INVENTION

In one embodiment, the invention relates to a chemical compound having formula 1:

1 wherein:

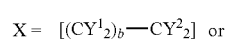

1A

1B $Y^1_2$ and $Y^2_2$ independently represent $H_2$ or $R^2_2$;
$R^1$ represents —C(O)— or —$CR^5R^6$—;
$R^2$, $R^3$, $R^4$, $R^5$, $R^6$, $R^7$, and $R^8$ represent:
- H or a branched or unbranched, saturated, acyclic hydrocarbon group having a minimum of 1 and a maximum of 24 carbon atoms;
- a minimum of 1 and a maximum of 8 $(CH_2CH_2O)_n$ or $(CH_2CH_2NH)_n$ groups;
- a saturated carbocyclic or heterocyclic hydrocarbon ring having a minimum of 3 and a maximum of 24 carbon atoms;
- a fused or unfused carbocyclic aryl ring having a minimum of 6 and a maximum of 20 carbon atoms; or
- a fused or unfused heterocyclic aryl ring having a minimum of 5 and a maximum of 20 carbon or heteroatoms (O or N), and
- wherein each ring of $R^2$, $R^3$, $R^4$, $R^5$, $R^6 R^7$, and $R^8$ is optionally substituted with one or more halo, nitro, hydroxyl, amino, $C_1$-$C_4$ alkylamino or dialkylamino, $C_1$-$C_6$ alkoxy, or a $C_1$-$C_4$ alkyl group;

x and y both equal 1 or x and y both equal 2;
m represents 0 or 1; and
Z represents $OR^7$, $SR^7$, $NR^7R^8$, or an active moiety.

In another embodiment, the invention relates to a polymer having the following formula:

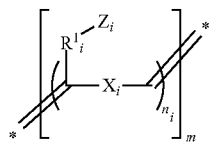

wherein:
m represents the number of blocks, and may be a minimum of 1, and a maximum of 100;
$n_i$ represents the number of monomers in a block, and may be a minimum of 1, and a maximum of 100; and
$R^1_i$, $X_i$, and $Z_i$ have the same definitions as $R^1$, X and Z, respectively, for the monomers in claim 1, are the same in each block, and may vary from block to block.

In yet another embodiment, the invention relates to a method for preparing the polymers described above, the method comprising:
(a) providing a chemical compound described in the first embodiment;
(b) providing a catalyst capable of promoting ring opening metathesis; and
(c) contacting the chemical compound with the catalyst under conditions that cause the chemical compound to polymerize into a polymer described above.

DETAILED DESCRIPTION OF THE INVENTION

Figure 1:
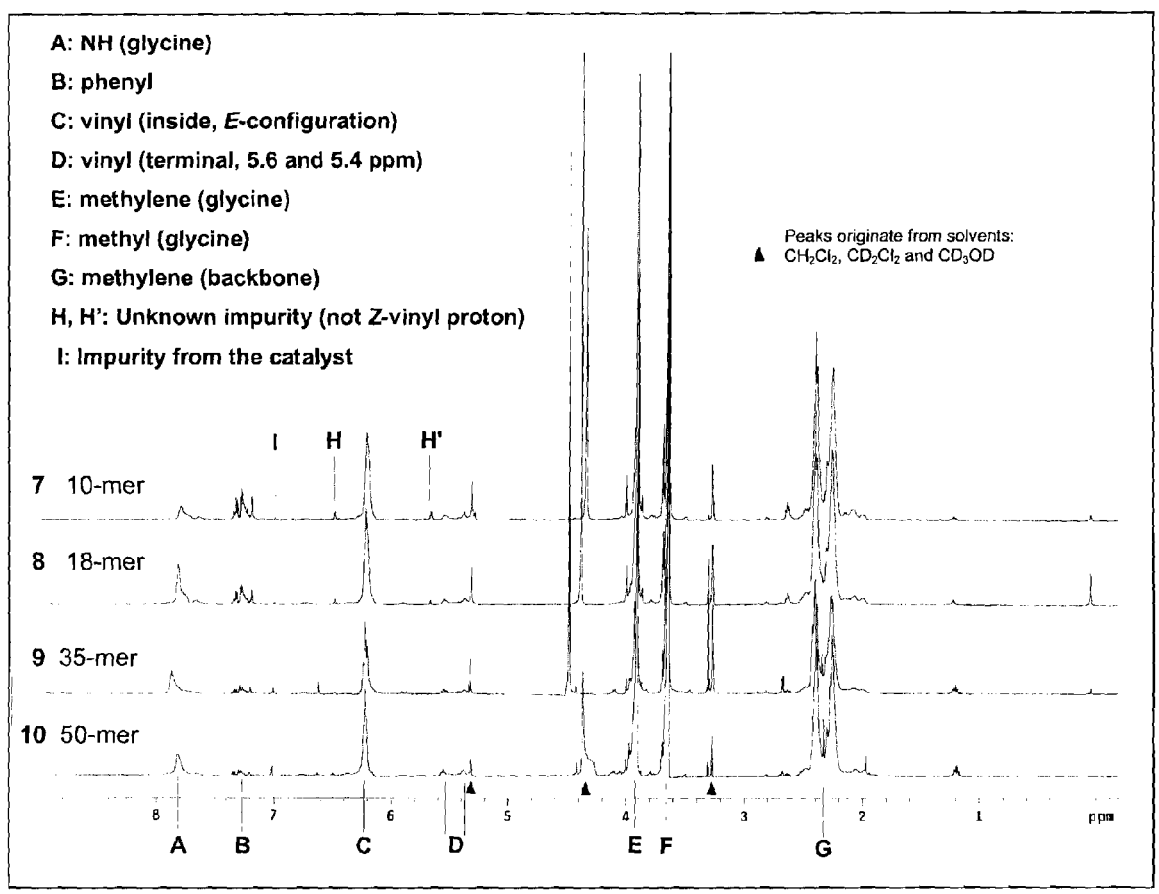
FIG. 1 shows a $^1$H-NMR spectra of ROMP polymers.
Figure 2:
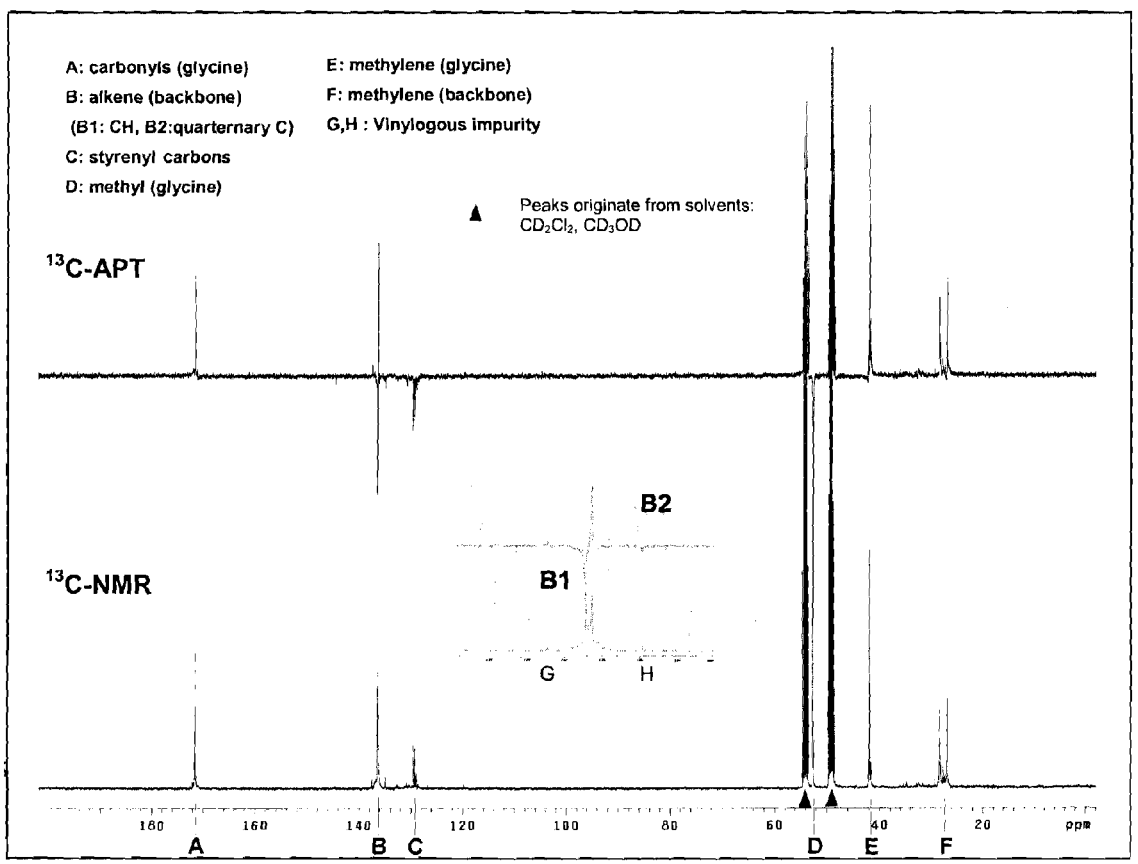
FIG. 2 shows a $^{13}$C-NMR and $^{13}$C-APT-NMR spectra of polymer 8.

The invention relates to stereoregular ROMP polymers, the monomers used to make them, and the processes used to convert the monomers to the polymers. The inventors have discovered that certain active moiety-containing ROMP polymers are surprising translationally invariant, although they are made using functional group-tolerant ruthenium catalysts. A polymer is considered to be translationally invariant when it is substantially all head-to-tail and E-olefinic. The word "substantially" in this context means within detection levels by NMR (typically up to 5% variation).

Monomers

The monomers used to make the stereoregular ROMP polymers have formula 1:

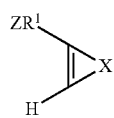

wherein:

$X = [(CY^1_2)_b—CY^2_2]$ or

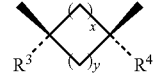

$Y^1_2$ and $Y^2_2$ independently represent $H_2$ or $R^2_2$. In other words, when b=1, $Y^1_2$ and $Y^2_2$ may both represent $H_2$, $Y^1_2$ and $Y^2_2$ may both represent $R^2_2$, or one of $Y^1_2$ and $Y^2_2$ may represent $H_2$ while the other represents $R^2_2$. $R^2_2$ represents two $R^2$ groups that may be any of the $R^2$ substituents listed below, and that are the same substituent on each carbon atom in order to avoid the existence of a chiral center, thereby preserving stereoregularity.

$R^1$ represents —C(O)— or —$CR^5R^6$—;
$R^2$, $R^3$, $R^4$, $R^5$, $R^6$, $R^7$, or $R^8$ represent H or a branched or unbranched, saturated, acyclic hydrocarbon group having a minimum of 1 and a maximum of 24 carbon atoms; a minimum of 1 and a maximum of 8 $CH_2CH_2O$ or $CH_2CH_2NH$ groups; a saturated non-aromatic carbocyclic or heterocyclic hydrocarbon ring having a minimum of 3 and a maximum of 24 carbon atoms; a fused or unfused carbocyclic aryl ring having a minimum of 6 and a maximum of 20 carbon atoms; or a fused or unfused heterocyclic aryl ring having a minimum of 5 and a maximum of 20 carbon or heteroatoms (O or N), and wherein each ring is optionally substituted with one or more halo (F, Cl, Br, or I), nitro, hydroxyl, amino, $C_1$-$C_4$ alkylamino or dialkylamino (e.g., methylamino, ethylamino, dimethylamino, diethylamino), $C_1$-$C_6$ alkoxy (e.g., methoxy, ethoxy), or a $C_1$-$C_4$ alkyl group (e.g., methyl, ethyl, isopropyl or t-butyl);

x and y both equal 1 or x and y both equal 2;
b represents 0 or 1; and
Z represents $OR^7$, $SR^7$, $NR^7R^8$, or an active moiety.
Preferably, $R^1$ represents —C(O)—. More preferably, $R^1$ represents —C(O)— and Z represents $OR^7$ or $NR^7R^8$. When Z represents $NR^7R^8$, $R^7$ preferably represents H.

For example, when $R^1$ represents —C(O)— and Z represents $OR^7$ or $NR^7R^8$, $R^1Z$ represents an ester or an amide. Preferred amides include amino acids, such as the twenty common naturally occurring amino residues, oligopeptides, peptides, and proteins. The amino acid residues include esters, such as methyl or ethyl esters.

In accordance with the above definitions, the monomers have no chiral centers, with the possible exception of $R^1$ and Z. Each of $R^1$ and Z may, or may not, have a chiral center.

In one embodiment, $R^2$, $R^3$, $R^4$, $R^5$, and $R^6$ represent H. In another embodiment, $R^2$, $R^3$, $R^4$, $R^5$, and $R^6$ represent $C_1$-$C_3$ alkyl or phenyl. In yet another embodiment, $R^2$, $R^3$, $R^4$, $R^5$, and $R^6$ represent methyl or ethyl.

In one embodiment, Z is a leaving group, wherein $R^7$ and $R^8$ represent, for example, N-succinimidyl or pentafluorophenyl. More specifically, when $R^1$ represents —C(O)— and Z represents $OR^7$, $R^7$ preferably represents pentafluorophenyl. When $R^1$ represents —C(O)— and Z represents $NR^7R^8$, $R^7$ and $R^8$ preferably join to form a succinimidyl ring.

The hydrocarbon groups described above have a minimum of one carbon atom. The hydrocarbon group contains a maximum of twenty-four carbon atoms. Preferably, the hydrocarbon group contains a maximum of eighteen, more preferably ten, even more preferably eight, and most preferably six carbon atoms. Optimally, the hydrocarbon group contains four carbon atoms.

In one embodiment, the hydrocarbon group is straight-chained, e.g., a saturated straight-chained alkyl group. Some examples of suitable saturated straight-chained alkyl groups include methyl, ethyl, n-propyl, n-butyl, n-pentyl, and n-hexyl groups.

The hydrocarbon group can alternatively be branched, i.e., a saturated branched alkyl group. Some examples of suitable saturated branched alkyl groups include iso-propyl, iso-butyl, sec-butyl, t-butyl, 1-methylbutyl, 2-methylbutyl, 3-methylbutyl (isopentyl), 1,1-dimethylpropyl, 1,2-dimethylpropyl, 2,2-dimethylpropyl (neopentyl), 1-methylpentyl, 2-methylpentyl, 3-methylpentyl, and 4-methylpentyl groups.

The hydrocarbon group can alternatively be saturated and cyclic, i.e., a cycloalkyl group. The cycloalkyl group preferably contains three to seven ring carbon atoms. Some examples of suitable cycloalkyl groups include cyclopropyl, cyclobutyl, cyclopentyl, cyclohexyl, and cycloheptyl groups.

The cyclic hydrocarbon group of $R^1$, $R^2$, $R^3$, and/or $R^4$ can, in addition, be aromatic, i.e., an aryl group. Preferably, the aryl group contains six to eighteen ring carbon atoms.

The aryl group can be fused or unfused. A preferred unfused aryl group is phenyl. Some examples of suitable fused aryl groups include naphthyl, phenanthryl, anthracenyl, triphenylenyl, chrysenyl, and pyrenyl.

The hydrocarbon groups described above can include one or more heteroatoms, e.g., nitrogen, oxygen, or sulfur atoms. Hydrocarbon chains that have heteroatoms include, for example, $-(CH_2CH_2T)_{m1}-$, wherein m1 represents 1-8, and T represents O, S or NH. Aryl groups that have heteroatoms can be fused or unfused, and include thiophenyl, furyl, pyrrolyl, pyrimidine, pyridazine, pyrazolyl, 1,4-diazanaphthalenyl, indolyl, pyridinyl, pyrazinyl imidazolyl, benzimidazolyl, 4,5-diazaphenanthrene, and benzoxazole.

Ring Opening Metathesis of Monomers

The monomers described above are subjected to ring opening metathesis to form the polymers of the invention. The polymerization is carried out by methods and under conditions well known in the art. Some suitable methods are described, for example, in Maynard, Heather D.; Okada, Sheldon Y.; Grubbs, Robert H. *Synthesis of Norbornenyl Polymers with Bioactive Oligopeptides by Ring-Opening Metathesis Polymerization*. Macromolecules (2000), 33(17), 6239-6248. Ilker, M. Firat; Coughlin, E. Bryan. *Alternating Copolymerizations of Polar and Nonpolar Cyclic Olefins by Ring-Opening Metathesis Polymerization*. Macromolecules (2002), 35(1), 54-58. C. Lapinte, Vincent; De Fremont, Pierre; Montembault, Veronique; Fontaine, Laurent. *Ring opening metathesis polymerization (ROMP) of cis- and trans-3,4-bis(acetyloxymethyl)cyclobut-1-enes and synthesis of block copolymers*. Macromolecular Chemistry and Physics (2004), 205(9), 1238-1245. Grubbs, Robert H. *The development of functional group tolerant ROMP catalysts*. Journal of Macromolecular Science, Pure and Applied Chemistry (1994), A31(11), 1829-33.

It should be noted that no distinction is made in this specification between polymerization and oligomerization. Any combination of two or more monomers is referred to herein as a polymerization.

Briefly, a monomer, as described above, is treated under suitable conditions with a catalyst capable of promoting ring opening metathesis in a suitable solvent. Suitable catalysts are described below. Suitable reaction conditions include temperatures of 20-50° C. under an inert atmosphere, such as under a nitrogen or argon atmosphere. Suitable solvents include, for example, $CH_2Cl_2$ or mixtures of $CH_2Cl_2$ and methanol, $CHCl_3$, toluene, diethyl ether, but preferably $CH_2Cl_2$.

Catalysts

Suitable catalysts for ring opening metathesis are well known in the art. The preferred catalysts are ruthenium catalysts. Suitable ruthenium catalysts are described in U.S. Pat. No. 5,998,326. The ruthenium catalysts described in U.S. Pat. No. 5,998,326 are incorporated herein by reference. Other suitable ruthenium catalysts are described in the references provided above in the section relating to Ring Opening Metathesis of Monomers. The ruthenium catalysts described in these references are incorporated herein by reference. The A preferred catalyst is the Grubbs' catalyst $[(H_2IMes)(3-BrPyr)_2(Cl)_2Ru=CHPh]$.

ROMP polymers

The polymer comprises m blocks, each of which comprises $n_i$ units of $=C(R^1_iZ_i)X_iCH=$. $R^1_i$, $X_i$, and $Z_i$ have the same definitions as $R^1$, X and Z, respectively, for the monomers; are the same in each block; and may vary from block to block. The total length of the polymer is the length of the sum of $n_i$ units. The sum of $n_i$ from i=1 to m is equal to or less than 100.

Preferably, $R^1_i$ represents —C(O)—. More preferably, $R^1_i$ represents —C(O)— and $Z_i$ represents $OR^7$ or $NR^7R^8$. When Z represents $NR^7R^8$, R7 preferably represents H. For example, when $R^1_i$ represents —C(O)— and $Z_i$ represents $OR^7$ or $NR^7R^8$, $R^1_iZ_i$ represents an ester or an amide. Preferred amides include amido groups include amino acids, such as the twenty common naturally occurring amino residues, oligopeptides, peptides, and proteins. The amino acid residues include esters, such as methyl or ethyl esters.

The repeating units of the polymers of the invention have the following formula:

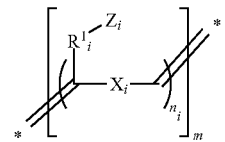

The polymer may be characterized as:

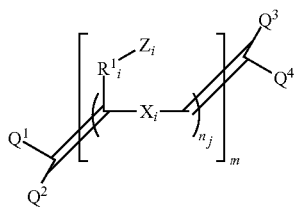

wherein:

m represents the number of blocks, and may be a minimum of 1, preferably 3, and more preferably 5. The maximum number of blocks is 100, and may also be 50, 30, 20, and 10. Some useful numbers of blocks include each of the 11 in the range of 10-20;

$n_i$ represents the number of monomers in a block, and may be a minimum of 1, 2, 3, or 5. The maximum number of monomers in a block is 100, 50, 30, 20, or 10. Some useful numbers of monomers in a block include each of the 11 numbers in the range of 10-20; and Q depends on the groups attached to the catalyst and on the unsaturated molecule used to quench the polymerization. For example, when the catalyst is Grubbs' catalyst [(H$_2$IMes)(PCy$_3$)(Cl)$_2$Ru=CHPh] and the quenching agent is ethyl vinyl ether, then Q1, Q2=H,H or H, OEt and Q3, Q4=Ph, H.

For example, the polymer might have three blocks, the first having two monomer units, the second having ten monomer units, and the third having two monomer units. Any other combination of numbers of blocks between 1 and 100 and numbers of units in a block between 1 and 100 is possible.

In one embodiment, i.e., when $R^1_i$ represents —C(O)—, and, where appropriate, $R^3$ and $R^4$ in formula 1B represent H and, where appropriate, one of $Y^1_2$ and $Y^2_2$ in formula 1A represents H$_2$, the polymer has the following formula:

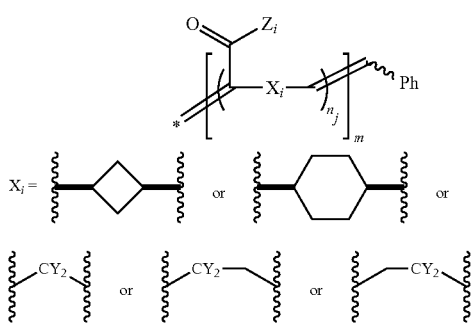

$Z_i$ = same as monomers, may vary from block to block
Y2 = H$_2$ or R$_2$
$n_j$ = 1-100
m = 1-100
i = 1 to m
The sum of $n_j$, from i = 1 to m, is ≤ 100

The polymer is constructed of m blocks, each of which is $n_i$ units of C(COZ$_i$)X$_i$CH in length and where each X$_i$ is independently any one of the 5 units specified in the Figure. Z$_i$ may be different in each block. Thus X$_i$ and Z$_i$ are the same units within a block and may vary from block to block. The total length of the polymer is Σ(n$_i$) units long.
i=1, m For example:

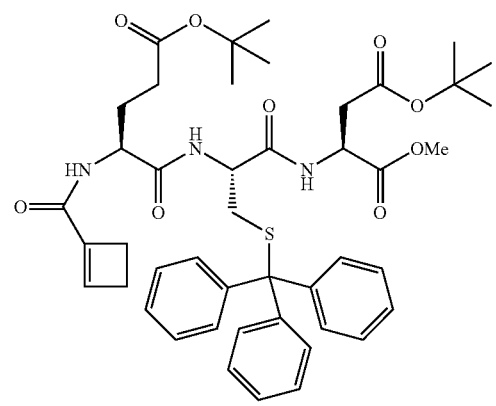

X$_1$, X$_2$ = CH$_2$

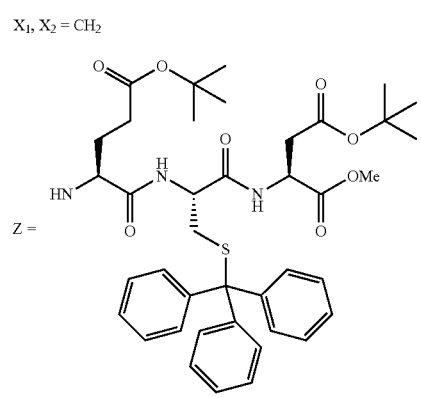

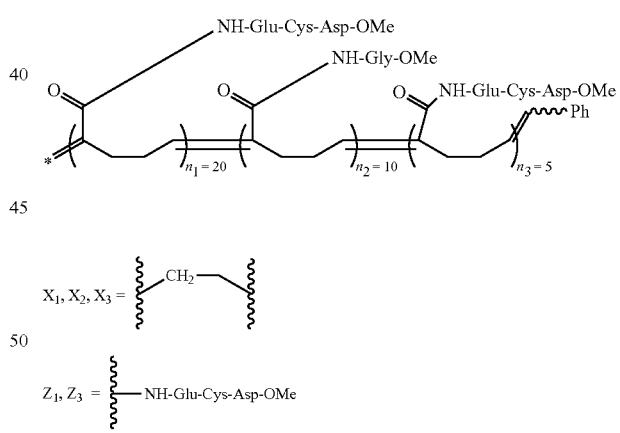

X$_1$, X$_2$, X$_3$ = —CH$_2$—

Z$_1$, Z$_3$ = —NH-Glu-Cys-Asp-OMe

Z$_2$ = —NH-Gly-OMe

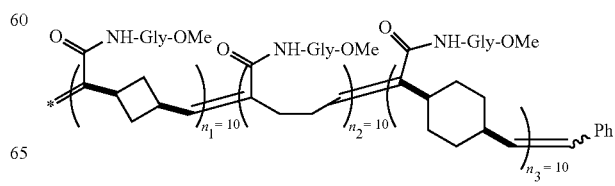

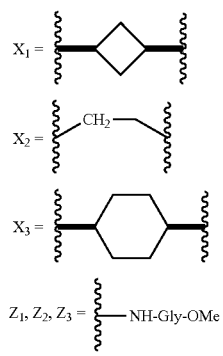
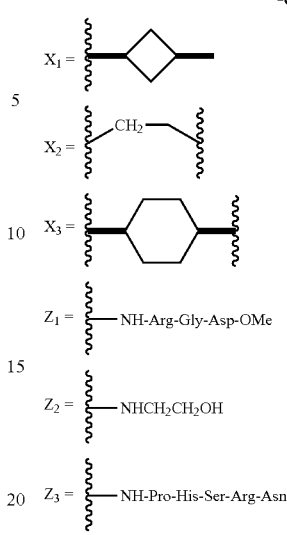
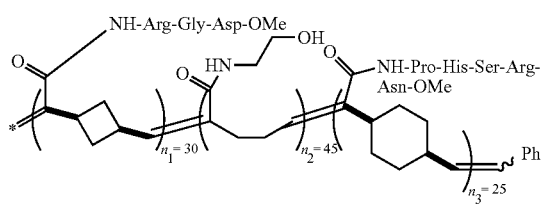
Some examples of stereoregular polymer blocks bearing active ligands that can be prepared from romp of cyclobutenecarboxylic acid amides.
| monomer |
|---|
| 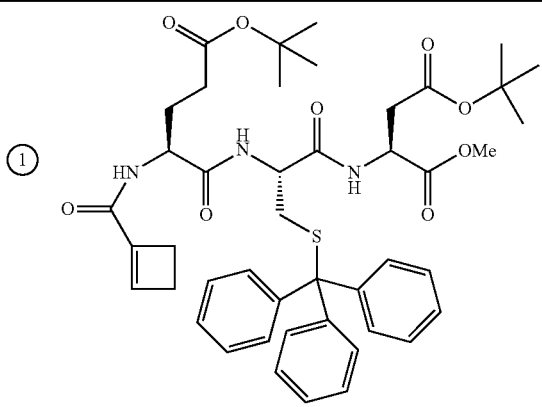 |
| protected peptide |
| 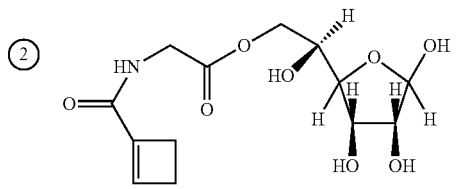 |
| sugar |

-continued
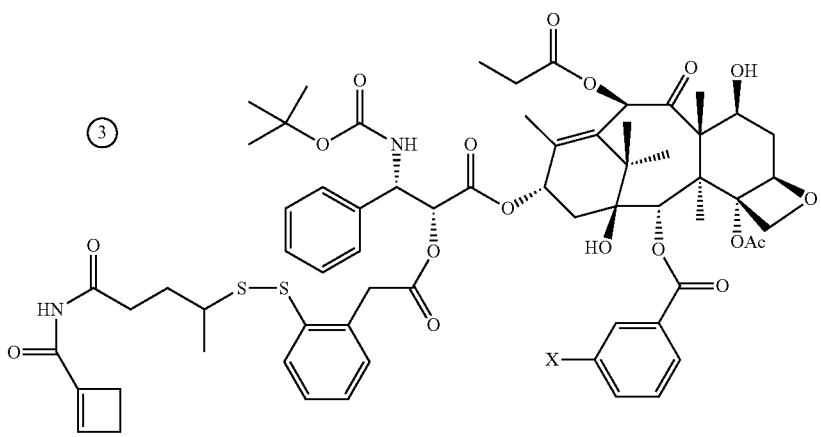
taxoid - drug delivery
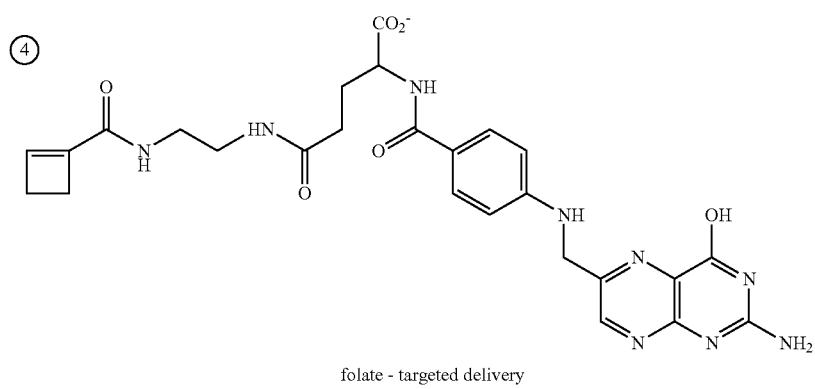
folate - targeted delivery
polymers as above with
$X_1, X_2 = CH_2$
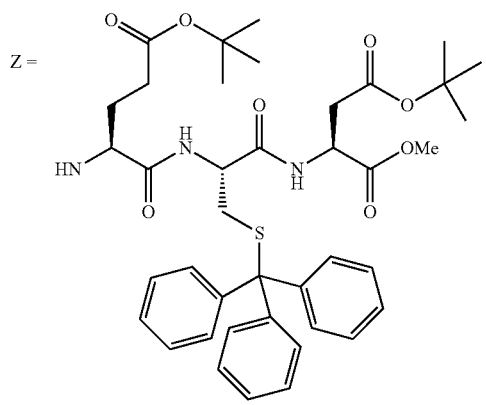
$X_2, X_2 = CH_2$
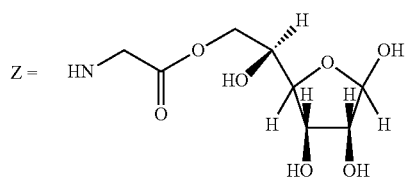

-continued

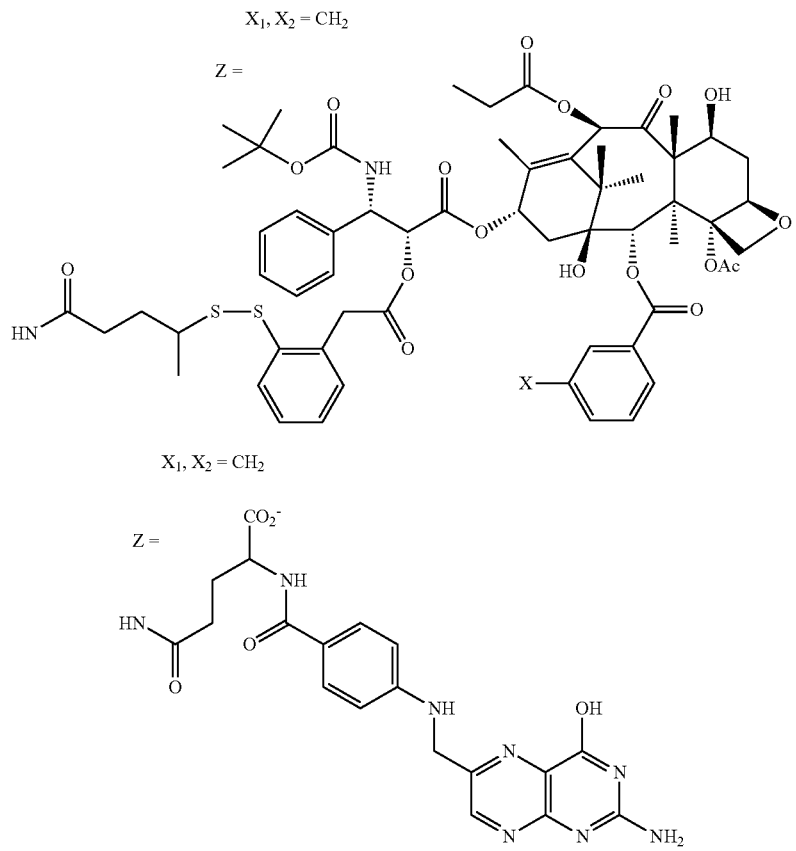

Active Moiety

In one embodiment, Z is an active moiety. The active moiety Z can be any moiety that can be attached to $R^1$, and that is useful for some purpose. The active moiety may, for example, have biological activity, and may have a pharmaceutical use. Alternatively, the active moiety is a co-factor, such as folic acid or a pharmaceutically acceptable salt (e.g., the sodium, potassium, calcium, ammonium salt) thereof (i.e., a folate).

The active moiety may also be an imaging agent. Some examples of imaging agents include fluorophores and biotin. Some examples of fluorophores include Cy3, Cy5, fluorescein, the Alexa dyes, and rhodamine.

Other useful imaging agents include, for example, precursors of metal complexes and metal complexes. Suitable precursors of metal complexes and metal complexes include those wherein the metal is iron, gadolinium, or technetium, such as DOTA. The complexes may, for example, be chelates of the metals, such as chelates of iron, gadolinium, or technetium. Iron complexes are; for example, suitable for ultrasound analyses. Gadolinium complexes are, for example, suitable for MRI. Technetium complexes are, for example, suitable for PET.

Preferably, the active moiety is a pharmacologically active agent. Pharmacologically active agents include any drug, compound, composition of matter or mixture e.g. therapeutic agents, diagnostic agents, or drug delivery agents, including targeting agents, which provides or is expected to provide some pharmacologic, often beneficial, effect that can be demonstrated in vivo or in vitro. The pharmacologically active agent is optionally suitable to be delivered to a subject, e.g., a human subject.

Such agents may include, for example, biological molecules, e.g. peptides, saccharides (monosaccharides disaccharides oligosaccharides having 3-8 saccharide units), nucleic acids, nucleosides, oligonucleotides, and lipids, or analogs thereof, as well as dyes, liposomes, microparticles, and therapeutic "small molecule" compounds. Examples of lipids include phospholipids, glycolipids, such as cerebrosides and gangliosides, sphingolipids, fatty diacylglycerides, triglycerides, glycosylglycerides, and steroids, including sterols, e.g., cholesterol. Nucleic acids and oligonucleotides include DNA and RNA. Nucleosides include deoxynucleosides.

A "small molecule" compound may be defined broadly as an organic, inorganic, or organometallic compound which is not a biomolecule as described above. Typically, such compounds have molecular weights of less than about 600.

Classes of therapeutic agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like. Some examples of antibiotics include penicillin and its derivatives, and tetracycline and its derivatives (e.g. doxycycline, minocycline, etc.). Some examples of anti-tumor agents include, for example, cisplatin, taxol, taxotere, methotrexate, and the anthracyclines, e.g., doxorubicin, idarubicin, daunorubicin, and epirubicin.

Certain functional groups, especially acidic and basic functional groups, are preferably protected during the polymerization reactions described herein. The protecting group can be essentially any of the well known groups suitable for the protection of functional groups. Suitable protecting groups are reviewed in *Protecting groups* by Kocienski, Philip J. Stuttgart; New York: Georg Thieme, c2005 and in *Protective groups in organic synthesis* by Greene, Theodora W. and Wuts, Peter G. M. New York: Wiley, c1999.

Any of the active moieties may be advantageously protected during the ROMP procedure. Such active moieties include, for example, therapeutic agents, folic acid, imaging agent, metal complex, metal chelating agent, precursor of a metal complex, such as a precursor of a complex of iron, gadolinium, or technetium, includes protected active moieties.

The active moiety may be attached directly to the monomer or polymer of the invention, ar may be attached by means of a linker (also known as a tether or a spacer). Any of the linkers known in the art may be used. For example, the linker may be a hydrocarbon chain, such as any of the acyclic hydrocarbon groups described above. Any of the carbon atoms may be replaced by heteroatoms, such as —O—, —S—, or —NH—. Some examples of heteroatom-containing hydrocarbon groups include the —(CH$_2$CH$_2$T)$_{m1}$- groups discussed above, e.g., hexaethyleneglycol. Oligopeptides and peptides can also be used as linkers, for example, oligopeptides and peptides having 2-20 amino acid residues. The linkers are preferably cleavable. An example of a cleavable linker is —CO(CH$_2$)$_2$SS(CH$_2$)$_2$NH—.

Utility

ROMP polymers provided have utility in a variety of fields, including not only polymer chemistry per se, but also in the pharmaceutical (Bertin et al., Macromolecules 37:8364-8372 (2000)), biomedical (Asgatay et al., Int. J. Pharm. 285:121-133 (2004); Non et al. Adv. Drug Delivery Rev. 57:609-636 (2005)), diagnostic and packaging industries. For example, ROMP-based nanoparticles with core structures composed of a chemically-linked chemotherapeutic agent, doxorubicin have been described. (Bertin et al., Chem. Commun. 3793-3795 (2005).) In addition, multivalent peptide-bearing ROMP polymers in which structural ambiguities are minimized may advantageously be used in studies of bi- and multidentate binding to cell surfaces. Such studies are described by Roberts, K. S.; Konkar, S.; Sampson, N. S. *ChemBioChem* 2003, 4, 1229-1231. Baessler, K.; Lee, Y.; Roberts, K. S.; Facompre, N.; Sampson, N. S. 2006 *Chem. Biol*, 16, 544-550. Roberts, K. S.; Sampson, N. S. *Org. Lett.* 2004, 6, 3253-5.

EXAMPLES

Synthesis of Monomers

Monomers for the ROMP of 1A (m=0, X=(CH$_3$)$_2$, R$^1$=CO, Z=protected amino acid or peptide) are prepared by coupling the known 3,3-dimethylcyclopropenecarboxylic acid (Baird, M. S.; Hussain, H. H.; Nethercott, W., "The preparation and lithiation of 1-halogenocyclopropenes," *J. Chem. Soc. Perkin Trans.* 1 (1986), 1845-1853) with the ligand Z by the activated ester (EDC) procedure.

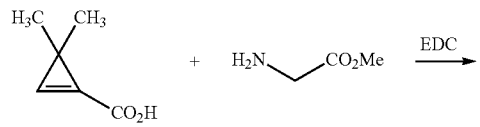

-continued

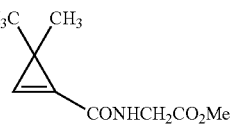

Alternatively, compounds in this series are prepared by the addition of 2-diazopropane to the corresponding acetylenic acid derivative and photolytic decomposition of the adduct (according to Baird, M. S.; Hussain, H. H., "The preparation and decomposition of alkyl 2-diazopent-4-enoates and 1-trimethylsilyl-1-diazobut-3-enes," *Tetrahedron* (1987), 43, 215-224 and Kohmoto, S.; Koyano, I.; Kishikawa, K.; Yamamoto, M.; Yamada, K., "Intramolecular photocycloaddition of cyclopropenes. Ring strain-driven hydrogen transfer of 1,4-biradical intermediates," *Tet. Lett.* (1996), 37, 8879-8882.)

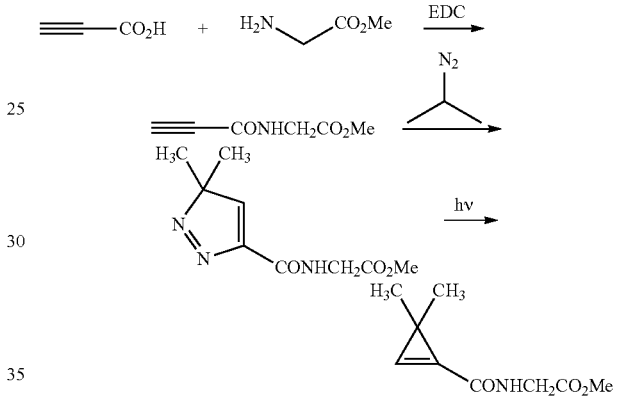

Monomers of structure 1B in which R$^3$ and R$^4$=H, x, y=2, R$^1$=CO, Z=protected amino acid or peptide) are prepared from the carboxylic acid shown below by the EDC method or via the acid chloride. See Wynn, C. M.; Vaughan, W. R., "Stereochemistry of pyrrolidine addition to bicyclo[2.2.2]oct-2-ene-2-carbonitrile," *J. Org. Chem.* (1968), 33, 2371 and Saha, S. L.; Roche, V. F.; Pendola, K.; Kearley, M.; Lei, L. P.; Romstedt, K. J.; Herdman, M.; Shams, G.; Kaisare, V.; Feller, D. R., "Synthesis and in vitro platelet aggregation and TP receptor binding studies on bicyclic 5,8-ethanooctahydroisoquinolines and 5,8-ethanotetrahydroisoquinolines," *Bioorg. Med. Chem. Lett.* (2002), 10, 2779-2793.

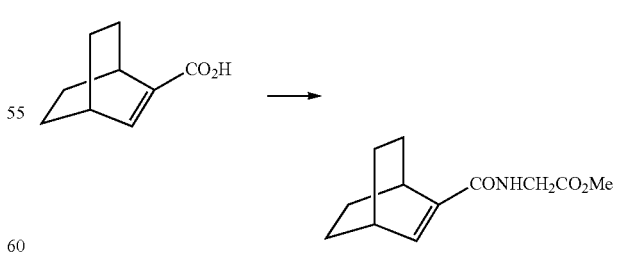

Monomers of structure 1B in which R3 and R4=H, x, y=1, R$^1$=CO, Z=protected amino acid or peptide) are prepared from the carboxylic acid shown below by the EDC method or via the acid chloride. The carboxylic acid is available by carboxylation of the corresponding vinyllithium reagent (prepared according to Newman-Evans, R. H.; Simon, R. J.; Carpenter, B. K., "The influence of intramolecular dynamics on branching ratios in thermal rearrangements," *J. Org. Chem.* (1990), 55, 695-711; see the experimental section).

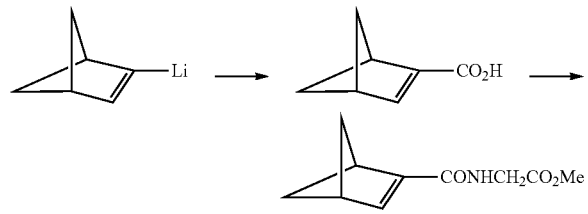

Synthesis of Polymers

General Information

Polymerization reactions were performed under an $N_2$ or Ar atmosphere. $CH_2Cl_2$ was dried over $CaH_2$ and distilled prior to use. $CD_2Cl_2$ was degassed before use for reactions. Grubbs' catalyst [($H_2$IMes)($PCy_3$)($Cl$)$_2$Ru=CHPh] and ethyl 1-bromocyclobutanecarboxylate were purchased from Aldrich (Cat # 56974-7 and 19729-7). The synthesis of precatalyst 2 was performed using the procedure published by Love, J. A. et al., *Angew. Chem. Int. Ed.* 2002, 41, 4035-4037.[1] Neutral alumina and Mallinckrodt silica gel 60 (230-400 mesh) were used for column chromatography. Aluminum TLC (thin layer chromatography) plates were silica gel 60 ($F_{254}$). $^1$H NMR spectra were reported as chemical shift in ppm (multiplicity, coupling constant in Hz, and integration) .$^{13}$C NMR spectra-were reported as chemical shift in ppm. The solvent peak was used as an internal reference.

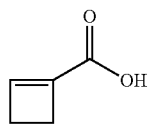

Cyclobut-1-enecarboxylie acid[2]

Cyclobut-1-enecarboxylic acid was prepared according to the procedure for preparation of 3,3-dimethylcylobutene carboxylic acid as described by Campbell et al., Campbell, A.; Rydon, H. N., *J. Chem. Soc.* 1953, 3002-3008, with minor modifications. KOH (6.00 g, 107 mmol) and toluene (90 mL) were mixed and then heated to reflux until the KOH dissolved. Ethyl 1-bromocyclobutanecarboxylate (4.90 g, 23.7 mmol) was added dropwise without heating. The reaction mixture was heated at reflux for 1 h, then cooled to RT. Cold water (60 mL) was added, the aqueous layer was washed with pentane (2×40 mL) and the pH was adjusted to 2.5 with 30% aq $H_2SO_4$. The product was then extracted from the aqueous layer with $Et_2O$ (4×40 mL) and dried over anhydrous $Na_2SO_4$. The $Et_2O$ was evaporated to give a yellow oil. The oil was dissolved in pentane (50 mL) and the upper layer was separated from the lower layer. The upper layer was cooled in an acetone-dry ice bath and stirred for 20 min. The resulting precipitate was filtered and dried under vacuum (1.14 g, 49% yield). The dried solid was stored at −20° C. to prevent decomposition. $^1$H-NMR (400 MHz, $CDCl_3$) δ 10.23 (bs, 1H), 6.94 (t, J=1.2 Hz, 1H), 2.76 (t, J=3.2 Hz, 2H), 2.51 (td, J=3.2 Hz, 1.2 Hz, 2H); $^{13}$C-NMR (100 MHz, $CDCl_3$) δ 167.5, 150.1, 138.4, 29.1, 27.5.

[(Cyclobut-1-enecarbonyl)-amino]-acetic acid methyl ester, (1)

Cyclobut-1-enecarboxylic acid (300 mg, 3.06 mmol), glycine methyl ester hydrochloride (423 mg, 3.37 mmol), and 1-(3-dimethylaminopropyl)-3-ethylcarbodiimide hydrochloride (704 mg, 3.67 mmol) were added to a round-bottomed flask. After addition of $CH_2Cl_2$ (6 mL) and N,N-diisopropylethylamine (1.07 mL, 6.12 mmol), the reaction mixture was stirred for 12 h at 24° C. When the reaction was complete, EtOAc (60 mL) was added and the resulting solution was washed with 1N aq HCl (3×20 mL) and 5% aq $NaHCO_3$ (3×20 mL). The combined aqueous HCl wash (60 mL) was re-extracted with ethyl acetate (2×30 mL). The combined organic solution was washed with the separated aqueous $NaHCO_3$ solution. The combined organic solution was dried over anhydrous $Na_2SO_4$. The solvent was evaporated and the residue was purified by neutral aluminum oxide column chromatography with 40% EtOAc/$CH_2Cl_2$ (216 mg, 42% yield). The purified fractions were concentrated and diluted with dry $CH_2Cl_2$ (3 mL) (complete concentration by vacuum should be avoided to prevent radical or ionic polymerization). In the solution state, monomer 1 is stable. For long term storage, the solution was kept at −80° C. to prevent possible decomposition. $^1$H-NMR (400 MHz, $CDCl_3$) δ 6.67 (t, J=1.2 Hz, 1H), 6.09 (br s, 1H), 4.11 (d, J=5.2 Hz, 2H), 3.78 (s, 3H), 2.73 (t, J=3.2 Hz, 2H), 2.49 (td, J=3.2 Hz, 1.2 Hz, 2H); $^{13}$C-NMR (100 MHz, $CDCl_3$) δ 170.6, 162.7, 141.5, 140.9, 52.5, 40.9, 28.6, 26.5; HRMS (ESI) calcd for $C_8H_{12}NO_3$ [M+H]$^+$ 170.0817, found 170.0809.

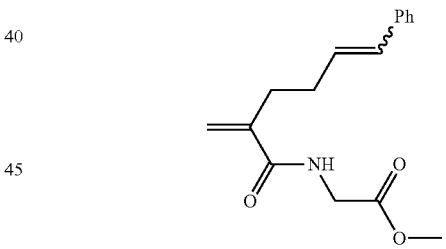

ROM (Ring Opening Metathesis) One-mer, (3).

Precatalyst 2 (71 mg, 0.080 mmol) was dissolved in $CH_2Cl_2$ (200 μL) under an Ar atmosphere. A solution of 1 (14 mg, 0.080 mmol) in $CH_2Cl_2$ (200 μL) was added to the catalyst solution. After 1 h, the reaction was quenched with ethyl vinyl ether (382 μL, 3.99 mmol). After evaporation of solvent, the residue was purified by silica gel column chromatography with 40% EtOAc/$CH_2Cl_2$ to obtain the ROM One-mer (mixture of E and Z isomers, 3 mg, 15% yield). $^1$H-NMR (500 MHz, $CD_3OD$) Z-isomer δ 7.31-7.17 (m, 5H), 6.44 (d, J=11.5 Hz, 1H), 5.70 (s, 1H), 5.66 (dt, J=11.5 Hz, 7.0 Hz, 1H) 5.38 (s, 1H), 3.93 (s, 2H), 3.70 (s, 3H), 2.50 (m, 4H); E-isomer δ 7.36-7.14 (m, 5H), 6.42 (d, J=15.5 Hz, 1H), 6.24 (dt, J=15.5 Hz, 7.0 Hz, 1H), 5.73 (s, 1H) 5.43 (s, 1H), 3.95 (s, 2H), 3.72 (s, 3H), 2.49 (s, 1H), J=7.5 Hz, 2H), 2.38 (q, J=7.0 Hz, 2H); $^{13}$C-NMR (100 MHz, $CD_3OD$) Z-isomer δ 172.0, 145.5, 139.0, 132.4, 130.9, 129.9, 129.6, 129.3, 119.9, 52.7, 42.2, 33.7, 28.4; E-isomer δ 172.0, 145.6, 139.3, 132.2, 130.5, 128.1, 127.8, 127.2, 120.1, 52.7, 42.2, 33.5, 32.9; HRMS (ESI) calcd for $C_{16}H_{20}NO_3$ $[M+H]^+$ 274.1443, found 274.1436.

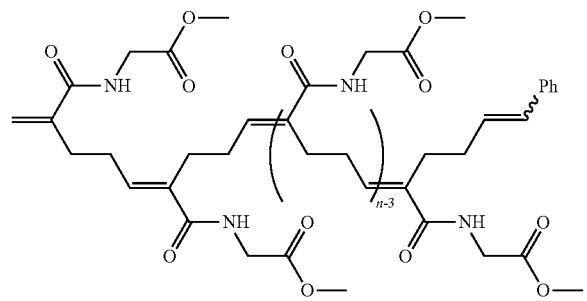

General Procedure for ROMP of 1

7: 10-mer

Under an $N_2$ atmosphere, precatalyst 2 (27 mg, 0.030 mmol) was dissolved in $CH_2Cl_2$ (1.8 mL). A solution of 51 mg of 1 in $CH_2Cl_2$ (600 μL) was added to the catalyst solution. The reaction mixture was stirred for 2 h at 24° C. and then the reaction was quenched with ethyl vinyl ether (300 μL, 3.13 mmol). After evaporation of solvent, 0.5 mL of $CH_2Cl_2$ was added to dissolve the residue and 2 ml of $Et_2O$ was added while stirring. The resulting sticky precipitate (48 mg, 89% yield) was further purified by silica gel column chromatography with 10% $MeOH/CH_2Cl_2$. The pure fractions were combined and dried under vacuum to yield 31 mg of the polymer (57% final yield).

8: 18-mer, 9: 35-mer and 10: 50-mer

For polymers longer than the 10-mer, 7, the polymerization procedure was slightly modified. Polymerizations were performed in an NMR tube and $CD_2Cl_2$ was used in order to monitor the reactions. For 9 and 10, the reaction mixtures were warmed to 40° C. after 5 min to increase the reaction rate. A summary of the reaction conditions is presented in Table 1.

TABLE 1

Reaction Summary

| Product | Rxn solvent | Rxn temp (° C.) | Rxn time (h) | % yield after precipitation (MC/diethyl ether) | % yield after silica column purification |
|---|---|---|---|---|---|
| 3, ROM One-mer | $CH_2Cl_2$ | 24 | 1.5 | — | 15 |
| 7, 10-mer | $CH_2Cl_2$ | 24 | 2 | 90 | 57 |
| 8, 18-mer | $CD_2Cl_2$ | 24 | 20 | 80 | 59 |
| 9, 35-mer | $CD_2Cl_2$ | 24-40 | 4 | 71 | 59 |
| 10, 50-mer | $CD_2Cl_2$ | 24-40 | 4 | 76 | 64 |

Characterization of the Polymers

The polymers were characterized by $^1H$ NMR, $^{13}C$ NMR, gHMQC, and $^{13}C$-APT spectroscopy.

Polymer 7: $^1H$-NMR (500 MHz, $CD_2Cl_2:CD_3OD/2:1$) δ 7.90~7.60 (bm, NH), 7.36~7.15 (m, 5H), 6.35~6.10 (bs, 11H), 5.56 (bs, 1H), 5.39 (bs, 1H), 4.03~3.84 (bs, 20H), 3.75~3.58 (bs, 30H) 2.55~2.10 (bm, 40H); $^{13}C$-NMR (100 MHz, $CD_2Cl_2:CD_3OD/2:1$) δ 171.7, 171.6, 136.4, 136.3, 133.0-128.5 (styrenyl carbons), 119.8, 52.6, 42.0, 28.4, 26.9. The gHMQC data is summarized in Table 2.

TABLE 2

$^1H$-NMR and $^{13}C$-NMR correlation of 7 using gHMQC spectroscopy.

| $^1H$-NMR (δ) | 7.29 | 6.22 | 3.91 | 3.65 | 2.39 | 2.25 |
|---|---|---|---|---|---|---|
| $^{13}C$-NMR (δ) | 129.3 | 136.4 | 42.0 | 52.6 | 26.9 | 28.4 |

Polymers 8, 9 and 10: The $^1H$-NMR and $^{13}C$-NMR spectra were the same as in polymer 7 except the relative integrations of peaks changed. The integration of the alkene peak at 6.22 ppm relative to the phenyl proton peak at 7.36-7.15 ppm increases as expected with the increasing length of the polymers. The integrations of the glycine (methylene and methyl protons) and backbone (methylene protons) protons also increase in the same way (FIG. 1). (A small doublet appears at δ 5.66 in the $^1H$ NMR spectrum of 7. The multiplicity of this peak is inconsistent with assignment to the Z-isomer. Moreover, the relative integration of this peak decreases as the polymer becomes longer. It appears to be an impurity arising from the catalyst. This impurity also appears in the $^{13}C$ NMR spectra at 137.4 ppm and 134.9 ppm. Again, the peak intensity decreases with increasing polymer length, consistent with it originating from catalyst.)

Polymer 8, $^{13}C$-APT: A $^{13}C$-APT spectrum of polymer 8 was acquired. (100 MHz, $CD_2Cl_2:CD_3OD/2:1$) δ 171.7 (quaternary C, carbonyl), 171.6 (quaternary C, carbonyl), 136.4 (CH, alkene), 136.3 (quaternary C, alkene), 133.0-128.5 (CH, styrenyl carbons), 119.7 ($CH_2$, terminal alkene), 52.6 ($CH_3$, methyl ester of glycine), 42.0 ($CH_2$, methylene of glycine), 28.4 ($CH_2$, methylene of backbone), 26.9 ($CH_2$, methylene of backbone).

In order to elucidate the geometry of the conjugated double bond(s), we prepared two trisubstituted unsaturated amides as model compounds for the (E) or (Z) units of the polymers; [(E)-2-methyl-but-2-enoylamino]-acetic acid methyl ester (11) and [(Z)-2-methyl-but-2-enoylamino]-acetic acid methyl ester (12). The chemical shift of the proton on carbon 3 in reference compound 11 is 6.47 ppm and in reference compound 12 is 5.65 ppm. Furthermore, the chemical shift of the proton on carbon 3 of (E)-N,2-dimethyl-2-butenamide is 6.29 ppm. Beak, P.; Kempf, D. J.; Wilson, K. D., *J. Am. Chem. Soc.* 1985, 107, 4745-4756.

The observed chemical shift of the alkene proton in polymers 7-10 is 6.22 ppm, and thus, these polymers are stereoregular with E stereochemistry.

[(E)-2-methyl-but-2-enoylamino]-acetic acid methyl ester, 11

(E)-2-methyl-2-butenoic acid (300 mg, 3.00 mmol) was dissolved in $CH_2Cl_2$ (6 mL) and N-methyl morpholine (396 μL, 3.60 mmol) was added to the solution. The reaction mixture was cooled to −15° C. Isobutyl chloroformate (389 μL, 3.00 mmol) was added and stirred at −15° C. for 15 min. Glycine methyl ester hydrochloride (377 mg, 3.00 mmol), $CH_2Cl_2$ (4 mL), and N-methyl morpholine (330 μL, 3.00 mmol) were added to the solution. After stirring at −15° C. for 15 min, the reaction mixture was warmed to 24° C. and stirred for 16 h. $CH_2Cl_2$ (60 mL) was added to the reaction mixture and the organic layer was washed with 1 N aq HCl (3×20 mL) and 5% aq $NaHCO_3$ (3×20 mL). The organic layer was dried over anhydrous $Na_2SO_4$ and the solvent was evaporated. The crude product was purified by silica gel column chromatography using 30% and 40% $EtOAc/CH_2Cl_2$ to give 11 (219 mg, 43% yield). $^1H$-NMR (400 MHz, $CDCl_3$) δ 6.47 (m, 1H), 6.37 (bs, 1H), 4.05 (d, J=4.8 Hz, 2H), 3.73 (s, 3H), 1.83 (m, 3H), 1.73 (m, 3H); $^{13}C$-NMR (100 MHz, $CDCl_3$) δ 170.8, 169.4, 131.8, 131.2, 52.4, 41.6, 14.0, 12.3; HRMS (ESI) calcd for $C_8H_{14}NO_3$ $[M+H]^+$ 172.0974, found 172.0974.

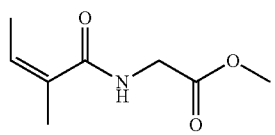

[(Z)-2-methyl-but-2-enoylamino]-acetic acid methyl ester, 12

[(Z)-2-methyl-but-2-enoylamino]-acetic acid methyl ester was prepared by coupling procedure above with (Z)-2-methyl-2-butenoic acid (300 mg, 3.00 mmol). Amide 12 was obtained after chromatography (219 mg, 45% yield). $^1$H-NMR (400 MHz; CDCl$_3$) δ 6.21 (bs, 1H), 5.65 (m, 1H), 4.07 (d, J=5.2 Hz, 1H), 4.06 (d, J=5.6 Hz, 1H), 3.73 (s, 3H), 1.86 (m, 3H), 1.81 (m, 3H); $^{13}$C-NMR (100 MHz, CDCl$_3$) δ 170.6, 170.2, 132.0, 129.3, 52.4, 41.1, 20.8, 15.2; HRMS (ESI) calcd for C$_8$H$_{14}$NO$_3$ [M+H]$^+$ 172.0974, found 172.0967.

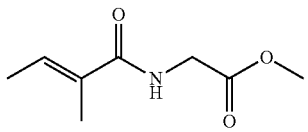

PDI (Poly Dispersity Index) Determination

Figure 3:
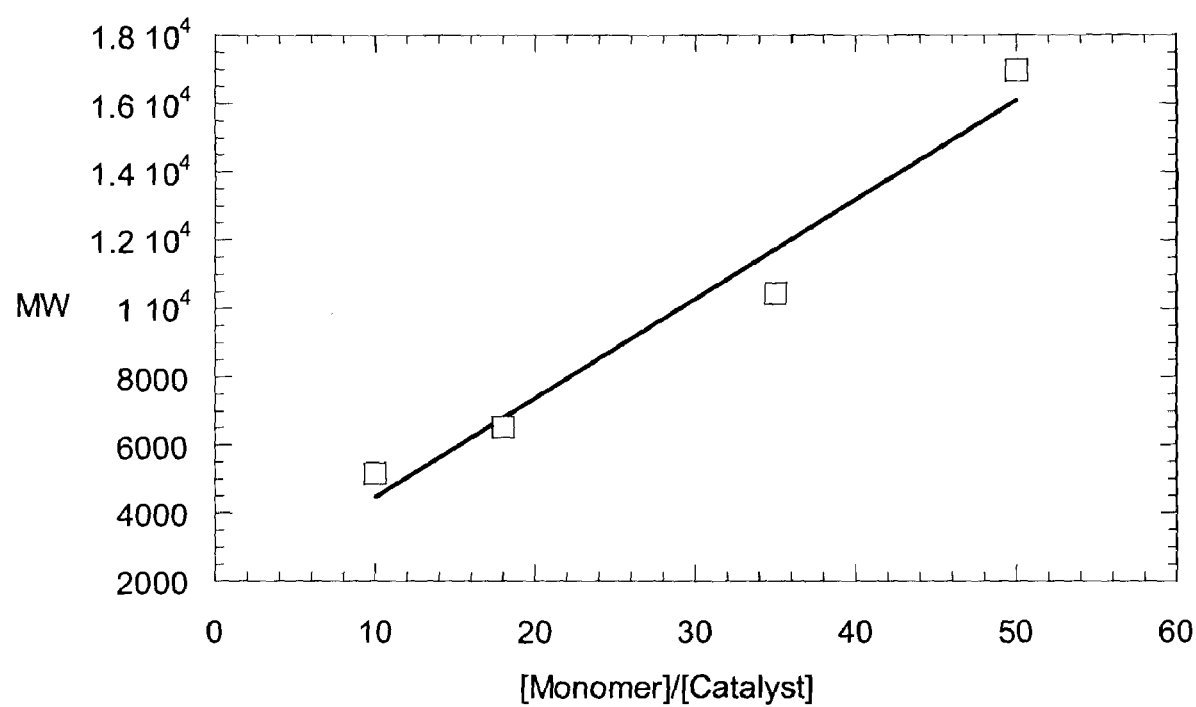
FIG. 3 shows a plot of molecular weight versus [Monomer]/[Catalyst] for polymers 7-10.

Purified polymers were dissolved in 10% MeOH/CH$_2$Cl$_2$ (0.25 mg/mL). An aliquot (50 µL) of the polymer solution was injected and analyzed by gel permeation chromatography using a Phenogel column (300×4.60 mm, 5 µm, linear mixed bed, 100-10$^7$ MW range). Elution was performed at 0.35 mL/min with CH$_2$Cl$_2$:MeOH (9:1) and detection at 240 nm at 24° C. Narrowly dispersed polystyrene standards from Aldrich were used as molecular weight calibrants. The number average and weighted average molecular weights were calculated from the chromatogram. The results are shown in Table 3. A plot of molecular weight versus [Monomer]/[Catalyst] is linear (FIG. 3).

TABLE 3

Polymerization results

| Polymer | [M]$_o$/[C] | Calcd M$_n$ | PSS M$_n$ | Temp ° C. | PDI | % Yield |
|---|---|---|---|---|---|---|
| 7 | 10/1 | 1,796 | 5,170 | 24 | 1.18 | 57 |
| 8 | 18/1 | 3,149 | 6,532 | 24 | 1.30 | 59 |
| 9 | 35/1 | 6,025 | 10,445 | 24-40 | 1.52 | 59 |
| 10 | 50/1 | 8,563 | 16,966 | 24-40 | 1.56 | 64 |

MALDI-TOF Mass Analysis

Figure 4:
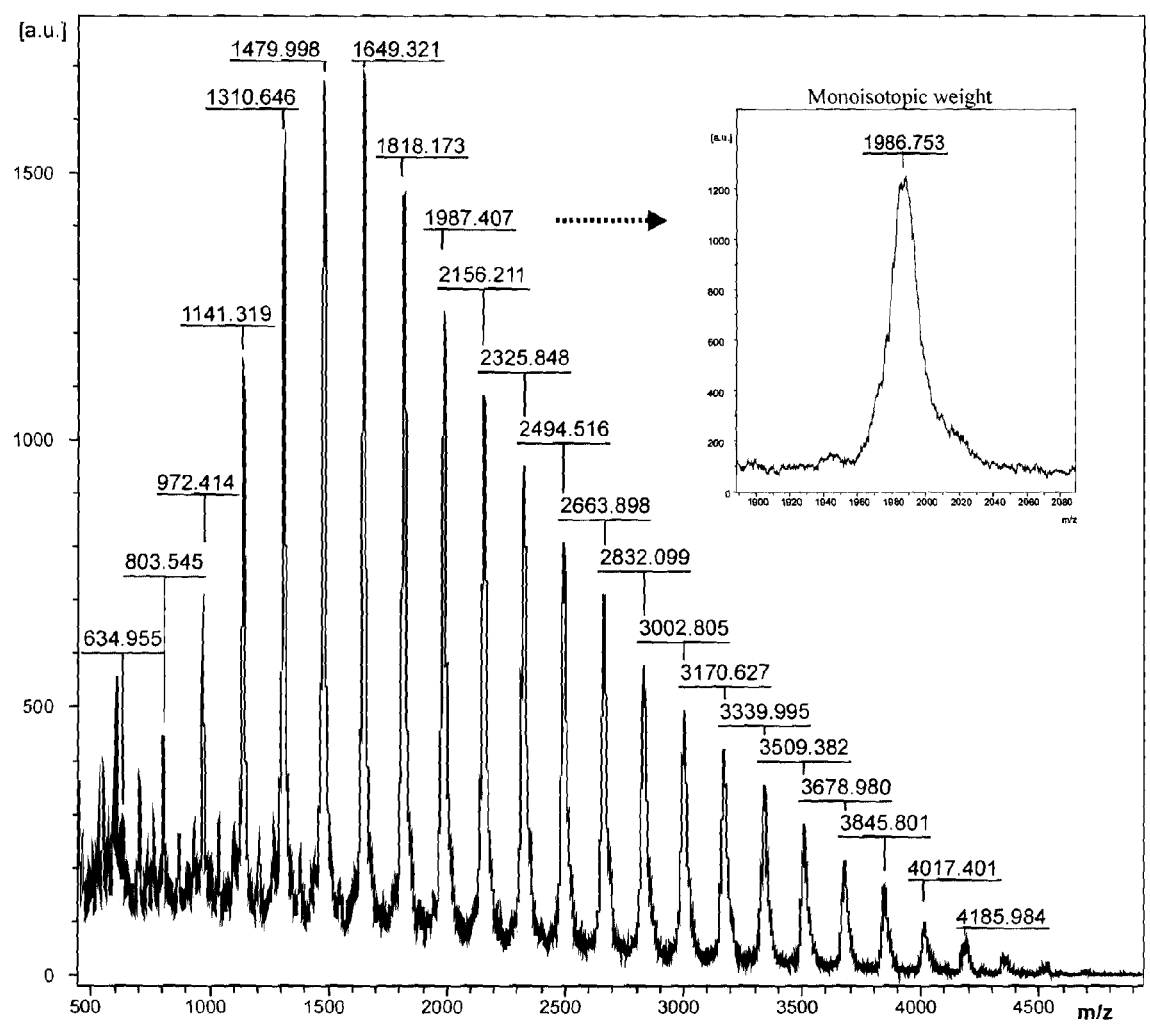
FIG. 4 shows a MALDI-TOF mass spectrum of polymer 7. (The inset shows the peaks corresponding to n=11, labeled with the monoisotopic mass/charge ratio.).

The 10-mer, 7, was analyzed by MALDI-TOF on an Autoflex TOF/TOF (Bruker Daltonics) and spectra were recorded in the linear mode without matrix suppression. 5-Chloro-2-mercaptobenzothiazole (CMBT) was used as the matrix, and a three point calibration was performed using angiotensin 11 (human, monoisotopic [M+H]$^+$: 1046.5423), ACTH fragment 18-39 (human, monoisotopic [M+H]$^+$: 2465.1989), and insulin (bovine, average [M+H]$^+$: 5734.51). The polymer was dissolved in 10% MeOH/CH$_2$Cl$_2$ at a concentration of 1 mg/mL. The matrix solution was prepared at a concentration of 4 mg/mL in 50% MeOH/CH$_2$Cl$_2$. The polymer was mixed in a ratio of 1/10 (v/v) with the matrix solution and 1 µL of the mixture was applied to the target surface and dried. FIG. 4 shows the spectrum with centroided mass/charge values. Only the [M+Na]$^+$ ions were observed. The mass of the residual end group was 104.6 which is consistent with the expected structure of 7. The number average molecular weight ($\overline{M}_n$) is 1935.29, the weight average molecular weight ($\overline{M}_w$) is 2230.44, the degree of polymerization is 11.45, and the PDI is 1.15 (calculated by PolyTools, Bruker) The calculated monoisotopic molecular weight for the 11-mer was 1986.82 [M+Na]$^+$ and the observed monoisotopic peak was 1986.75 [M+Na]$^+$ (FIG. 4, inset).

Cyclobut-1-enecarboxylic acid (3.0 mmol), oxalyl chloride (4.5 mmol) were stirred in CH$_2$Cl$_2$ (6 mL) for 1 h at 0° C. When the reaction was complete the solvent was evaporated and the residue was dissolved in CH$_2$Cl$_2$ at 0° C. Aminoethanol (4.5 mmol), diisopropylamine (4.5 mmol) and dimethylamino pyridine (0.15 mmol) were added to the acid chloride solution and the reaction allowed to warm to rt slowly. When the reaction was complete, EtOAc (60 mL) was added and the resulting solution was washed with 1N aq HCl (3×20 mL) and 5% aq NaHCO$_3$ (3×20 mL). The combined aqueous HCl wash (60 mL) was re-extracted with ethyl acetate (2×30 mL). The combined organic solution was washed with the separated aqueous NaHCO$_3$ solution. The combined organic solution was dried over anhydrous Na$_2$SO$_4$. The solvent was evaporated and the residue was purified by flash chromatography with 40% EtOAc/CH$_2$Cl$_2$. The purified fractions were concentrated and diluted with dry CH$_2$Cl$_2$ (3 mL) and stored at −20° C.

General Procedure for ROMP of Cyclobutene Monomers.

A reaction vessel was evacuated for 15 min, then filled with Ar for 15 min. Under an Ar atmosphere, a solution of monomer (0.06 mmol) in CD$_2$Cl$_2$ (300 µL) was added to the vessel. Then a solution of precatalyst [(H$_2$IMes)(3-BrPyr)$_2$(Cl)$_2$Ru═CHPh] (0.006 mmol) in CD$_2$Cl$_2$ (300 µL), was added to the monomer solution. After complete mixing of the solution, the reaction was monitored by $^1$H-NMR spectroscopy at 400 or 500 MHz at 25° C. until all the monomer was consumed. Then the reaction was quenched with ethyl vinyl ether (50 µL) for 1 h. Stereoregularity was assessed by monitoring the alkenyl region of the polymer $^1$H-NMR spectrum. A single alkenyl peak at 6.0-6.2 ppm indicated that the substantially all E, head-tail polymer was formed in a stereoregular fashion. The results are shown in Table 4. The structures of monomers 13-20 are shown below the table.

TABLE 4

Synthesis of ROMP polymers from cyclobutene monomers

| Monomer | Monomer:catalyst | Monomer (M) | Solvent | % Conversion | Reaction Time (h) | Reaction Temp (° C.) | Chemical shift (ppm) of polymer alkene |
|---|---|---|---|---|---|---|---|
| 13 | 3:1 | 0.06 | CD$_2$Cl$_2$ | 92% | 3 | 25 | 6.3 |
| 14 | 10:1 | 0.25 | CH$_2$Cl$_2$/CH$_3$OH (3/1) | 60% | 4 | r.t. or 30 | 6.21 |

TABLE 4-continued
Synthesis of ROMP polymers from cyclobutene monomers
| Monomer | Monomer:catalyst | Monomer (M) | Solvent | % Conversion | Reaction Time (h) | Reaction Temp (° C.) | Chemical shift (ppm) of polymer alkene |
|---|---|---|---|---|---|---|---|
| 15 | 10:1 | 0.16 | CH$_2$Cl$_2$ | >90% | 2 | r.t. | 6.2 |
| 16 | 10:1 | 0.09 | CH$_2$Cl$_2$/CH$_3$OH (3/1) | ~30% | 4 | r.t. | 6.25 |
| 17 | 10:1 | 0.1 | CD$_2$Cl$_2$ | 96% | 1.3 | 25 | 6.36 |
| 18 | 10:1 | 0.1 | CD$_2$Cl$_2$ | 98% | 7 | 25 | 6.25 |
| 1 | 10:1 | 0.1 | CD$_2$Cl$_2$ | 91% | 3 | 25 | 6.22 |
| 19 | 10:1 | 0.1 | CD$_2$Cl$_2$ | 86% | 4 | 25 | 6.18 |
| 20 | 10:1 | 0.1 | CD$_2$Cl$_2$ | 96% | 6 | 25 | 6.15 |
13 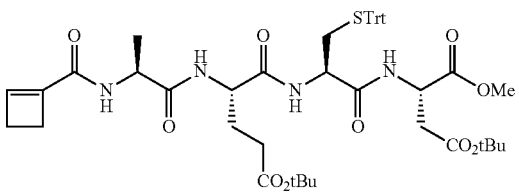
14 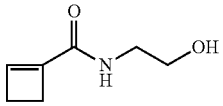
15 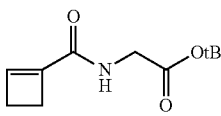
16 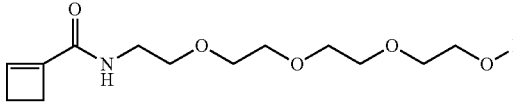
17 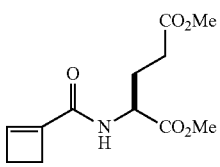
18 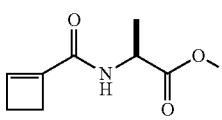
19 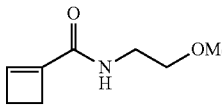
20 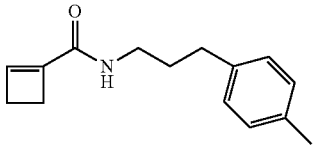

What we claim is:

1. A chemical compound having formula 1:

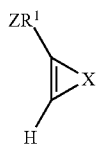

1 wherein:

$X = [CY^1_2)_b—CY^2_2]$ or

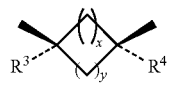

1A

1B $Y^1_2$ and $Y^2_2$ independently represent $H_2$ or $R^2_2$;
$R^1$ represents —C(O)— or —$CR^5R^6$—;
$R^2$, $R^3$, $R^4$, $R^5$, $R^6$ $R^7$, and $R^8$ represent:
  H or a branched or unbranched, saturated, acyclic hydrocarbon group having a minimum of 1 and a maximum of 24 carbon atoms;
  a minimum of 1 and a maximum of 8 $(CH_2CH_2O)_n$ or $(CH_2CH_2NH)_n$ groups;
  a saturated carbocyclic or heterocyclic hydrocarbon ring having a minimum of 3 and a maximum of 24 carbon atoms;
  a fused or unfused carbocyclic aryl ring having a minimum of 6 and a maximum of 20 carbon atoms; or
  a fused or unfused heterocyclic aryl ring having a minimum of 5 and a maximum of 20 carbon or heteroatoms (O or N), and
  wherein each ring of $R^2$, $R^3$, $R^4$, $R^5$, $R^6$ $R^7$, and $R^8$ is optionally substituted with one or more halo, nitro, hydroxyl, amino, $C_1$-$C_4$ alkylamino or dialkylamino, $C_1$-$C_6$ alkoxy, or a $C_1$-$C_4$ alkyl group;
x and y both equal 1 or x and y both equal 2;
b represents 0 or 1; and
Z represents $OR^7$, $SR^7$, $NR^7R^8$, or an active moiety.

2. A chemical compound according to claim 1, wherein $R^1$ represents —C(O)—.

3. A chemical compound according to claim 2, wherein Z represents $OR^7$ or $NR^7R^8$.

4. A chemical compound according to claim 3, wherein Z represents $NR^7R^8$, and $R^7$ represents H.

5. A chemical compound according to claim 4, wherein $R^1Z$ represents an amino acid.

6. A chemical compound according to claim 4, wherein $R^1Z$ represents an oligopeptide, a peptide, or a protein.

7. A chemical compound according to claim 1, wherein $R^2$, $R^3$, $R^4$, $R^5$, and $R^6$ represent H.

8. A chemical compound according to claim 1, wherein $R^2$, $R^3$, $R^4$, $R^5$, and $R^6$ represent $C_1$-$C_3$ alkyl or phenyl.

9. A chemical compound according to claim 8, wherein $R^2$, $R^3$, $R^4$, $R^5$, and $R^6$ represent methyl or ethyl.

10. A chemical compound according to claim 1, wherein $R^1$ represents —C(O)—, Z represents $OR^7$, and $R^7$ represents pentafluorophenyl.

11. A chemical compound according to claim 1, wherein $R^1$ represents —C(O)—, Z represents $NR^7R^8$, and $R^7$ and $R^8$ join to form a succinimidyl ring.

12. A chemical compound according to claim 1, wherein Z represents a biological molecule.

13. A chemical compound according to claim 12, wherein the biological molecule is a peptide having 2-8 amino acid residues.

14. A chemical compound according to claim 12, wherein the biological molecule is a saccharide.

15. A chemical compound according to claim 13, wherein the saccharide is a monosaccharides, disaccharides, or oligosaccharides having 3-8 saccharide units.

16. A chemical compound according to claim 12, wherein the biological molecule is a nucleoside or an oligonucleotide having 1-8 nucleotides.

17. A chemical compound according to claim 12, wherein the biological molecule is a fatty acid.

18. A chemical compound according to claim 1, wherein Z represents a small molecule.

19. A chemical compound according to claim 1, wherein the small molecule is a pharmacologically active agent.

20. A chemical compound according to claim 19, wherein the small molecule is an anti-tumor agent.

21. A chemical compound according to claim 18, wherein the small molecule is a co-factor.

22. A chemical compound according to claim 21, wherein the co-factor is folic acid, a pharmaceutically acceptable salt thereof.

23. A chemical compound according to claim 18, wherein the small molecule is an imaging agent.

24. A chemical compound according to claim 23, wherein the imaging agent is a metal complex.

25. A chemical compound according to claim 23, wherein the imaging agent is a precursor of a metal complex.

26. A chemical compound according to claim 23, wherein the imaging agent is a metal chelating agent.

27. A chemical compound according to claim 24, wherein the complex is a complex of iron, a complex of gadolinium, or a chelate of technetium.

28. A chemical compound according to claim 27, wherein the complex is a chelate of technetium that is DOTA.

29. A chemical compound according to claim 23, wherein the imaging agent is a fluorophore or biotin.

30. A polymer having the following formula:

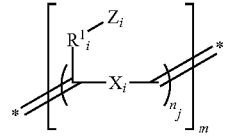

wherein:
  m represents the number of blocks, and may be a minimum of 1, and a maximum of 100;
  $n_i$, represents the number of monomers in a block, and may be a minimum of 1, and a maximum of 100; and
  $R^1_i$, $X_i$, and Z, have the same definitions as $R^1$, X and Z, respectively, for the monomers in claim 1, are the same in each block, and may vary from block to block.

31. A method for preparing the polymers of claim 30, the method comprising:
  (a) providing a chemical compound described in claim 1;
  (b) providing a catalyst capable of promoting ring opening metathesis; and (c) contacting the chemical compound with the catalyst under conditions that cause the chemical compound to polymerize into a polymer.

32. A method according to claim 31, wherein the catalyst comprises ruthenium.

33. A method according to claim 31, wherein the catalyst is [(H$_2$IMes)(3-BrPyr)$_2$(Cl)$_2$Ru═CHPh].

* * * * *

UNITED STATES PATENT AND TRADEMARK OFFICE
CERTIFICATE OF CORRECTION

PATENT NO. : 8,232,360 B2
APPLICATION NO. : 12/309503
DATED : July 31, 2012
INVENTOR(S) : Sampson et al.

It is certified that error appears in the above-identified patent and that said Letters Patent is hereby corrected as shown below:

IN THE SPECIFICATION:

Column 1, lines 6-8:

Now reads: "This invention was funded by the National Institutes of Health under grants HD38519 and CA87503. The United States government has rights in this application."

Should read: -- This invention was made with government support under grant numbers HD38519 and CA87503 awarded by the National Institute of Health. The government has certain rights in the invention. --

Signed and Sealed this
Twenty-third Day of October, 2012

David J. Kappos
*Director of the United States Patent and Trademark Office*